US009389210B2

(12) United States Patent
Ooga (10) Patent No.: US 9,389,210 B2
(45) Date of Patent: Jul. 12, 2016

(54) THERMAL DISTRIBUTION DISPLAY

(71) Applicant: FUJIFILM CORPORATION, Minato-ku, Tokyo (JP)

(72) Inventor: Kunihiko Ooga, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 274 days.

(21) Appl. No.: 14/178,280

(22) Filed: Feb. 12, 2014

(65) Prior Publication Data

US 2014/0161684 A1 Jun. 12, 2014

Related U.S. Application Data

(63) Continuation of application No. PCT/JP2012/068507, filed on Jul. 20, 2012.

(30) Foreign Application Priority Data

Aug. 17, 2011 (JP) ................................. 2011-178440

(51) Int. Cl.
  *G01N 31/22* (2006.01)
  *B41M 5/34* (2006.01)
  (Continued)

(52) U.S. Cl.
  CPC ............... *G01N 31/229* (2013.01); *B41M 5/34* (2013.01); *G01K 11/16* (2013.01); *B41M 5/30* (2013.01); *B41M 5/3275* (2013.01); *B41M 5/3335* (2013.01)

(58) Field of Classification Search
  CPC ...................................................... G01N 31/22
  USPC .................................. 422/425; 436/1–2, 166
  See application file for complete search history.

(56) References Cited

U.S. PATENT DOCUMENTS 3,983,292 A * 9/1976 Saito ..................... B41M 5/155
                                                               503/212
4,636,819 A * 1/1987 Nagamoto ............... B41M 5/32
                                                               427/151
(Continued)

FOREIGN PATENT DOCUMENTS

JP    H05-52666 A      3/1993
JP    2004-117145 A    4/2004
WO    2010/090213      8/2010

OTHER PUBLICATIONS

Written Opinion of the ISA issued in International Application No. PCT/JP2012/068507 on Sep. 4, 2012.

(Continued)

*Primary Examiner* — Arlen Soderquist
(74) *Attorney, Agent, or Firm* — SOLARIS Intellectual Property Group, PLLC (57) ABSTRACT

Provided is a thermal distribution display including, on a support, a thermal distribution display layer that includes at least two electron-donating dye precursors that develop mutually different color tones, the dye precursors including at least one electron-donating dye precursor that decomposes in a temperature range of 190° C. or higher to undergo a change in hue; at least one electron-accepting compound that allows the at least two electron-donating dye precursors to develop colors; and a binder, wherein, in the thermal distribution display layer, a temperature $T_{0.2}$, at which a density is 0.2 greater than a background density, satisfies the following formula (1).

$$\frac{0.2}{T_{0.2} - T_{min}} \leq 0.02 \qquad \text{Formula (1)}$$

8 Claims, 2 Drawing Sheets

(51) Int. Cl.
*G01K 11/16* (2006.01)
*B41M 5/30* (2006.01)
*B41M 5/327* (2006.01)
*B41M 5/333* (2006.01)

(56) References Cited

U.S. PATENT DOCUMENTS

| | | | | |
|---|---|---|---|---|
| 4,727,054 A * | 2/1988 | Yuyama | B41M 5/44 | 427/152 |
| 4,727,056 A * | 2/1988 | Sano | B41M 5/1455 | 427/150 |
| 4,803,192 A * | 2/1989 | Saeki | B41M 5/145 | 427/151 |
| 4,849,397 A * | 7/1989 | Sano | B41M 5/132 | 427/151 |
| 4,918,045 A * | 4/1990 | Matsuoka | B41M 5/1655 | 427/151 |
| 4,980,337 A * | 12/1990 | Kawasaki | B41M 5/44 | 427/152 |
| 5,094,999 A * | 3/1992 | Tsuchida | B41M 5/3336 | 427/150 |
| 5,187,143 A * | 2/1993 | Watanabe | B41M 5/3335 | 503/212 |
| 5,236,883 A * | 8/1993 | Nakazawa | B41M 5/42 | 427/152 |
| 5,286,703 A * | 2/1994 | Wachi | B41M 5/327 | 427/152 |
| 5,691,271 A * | 11/1997 | Yanagihara | B41M 5/327 | 503/204 |
| 5,731,262 A * | 3/1998 | Ogino | B41M 5/3375 | 503/200 |
| 5,753,588 A * | 5/1998 | Iida | B41M 5/327 | 503/208 |
| 5,880,064 A * | 3/1999 | Kagota | B41M 5/145 | 503/213 |
| 5,935,900 A * | 8/1999 | Meguro | B41M 5/3375 | 427/152 |
| 6,921,740 B1 * | 7/2005 | Hizatate | B41M 5/3333 | 503/200 |
| 7,040,929 B2 * | 5/2006 | Defieuw | G03C 1/4989 | 430/523 |
| 7,153,812 B2 * | 12/2006 | Hara | B41M 5/42 | 503/200 |
| 2001/0044553 A1 * | 11/2001 | Kabashima | B41M 5/155 | 560/157 |
| 2006/0116288 A1 * | 6/2006 | Mori | B41M 5/3335 | 503/216 |
| 2006/0205594 A1 * | 9/2006 | Mitamura | B41M 5/3375 | 503/215 |
| 2011/0287548 A1 | 11/2011 | Ozawa | | |

OTHER PUBLICATIONS

International Search Report issued in International Application No. PCT/JP2012/068507 on Sep. 4, 2012.

English language translation of the following: Office action dated Nov. 15, 2014 from the SIPO in a Chinese patent application corresponding to the instant patent application. This office action translation is submitted now in order to supplement the understanding of the cited references which are being disclosed in the instant Information Disclosure Statement.

* cited by examiner

THERMAL DISTRIBUTION DISPLAY

CROSS-REFERENCE TO RELATED APPLICATIONS

This application is a continuation application of International Application No. PCT/JP2012/068507, filed Jul. 20, 2012, which is incorporated herein by reference. Further, this application claims priority from Japanese Patent Application No. 2011-178440, filed Aug. 17, 2011, which is incorporated herein by reference.

TECHNICAL FIELD

The present invention relates to a thermal distribution display using an electron-donating dye precursor.

BACKGROUND ART

A hot pressing method has been known as a method intended for bonding of sheets or heat transfer of a transfer layer coated on a film. For example, in the case of performing hot pressing, such as bonding or heat sealing of an anisotropic conductive film (ACF) or bonding of electronic components such as FPC, thermal distribution in the press surfaces may affect the quality of manufactured products.

On the occasion of manufacturing by performing hot pressing, in order to enhance the quality of manufactured products and to shorten the tact time required in manufacturing, it is important to manage the temperature and the temperature distribution at the hot-press surfaces to attain adequate values. In order to do so, an operation of measuring the actual temperature and regulating the temperature according to the temperature distribution that has occurred, is required.

However, for the tracing of the temperature distribution in pressed surfaces, a method of measuring the temperature by interposing, between hot pressed surfaces, a pseudo-surface temperature sensor that is formed by disposing a number of thermocouples, resistance temperature detectors, thermistors or the like on a sheet or a plate member, has been carried out (see, for example, Japanese Patent Application Laid-Open (JP-A) No. H5-52666).

Furthermore, as a sheet or method for checking the temperature of a large hot surface, there has been suggested a temperature measurement method that is carried out by providing a hot pressing process of superposing a thermosensitive sheet on an article to be processed or within the material of the article, supplying the article between hot-press surfaces that face each other, and performing hot pressing; a density measurement process of measuring the density of measurement sites at the thermosensitive sheet after performing hot pressing; and a temperature calculation process of calculating the heating temperature of the hot press based on the density thus measured (see, for example, JP-A No. 2004-117145).

Furthermore, in recent years, a thermal distribution measurement film (THERMOSCALE) that develops black color when heat is applied thereto has been marketed, and a method which allows investigation of the heat quantity distribution of a contacting surface has been provided.

PRIOR ART DOCUMENTS

Patent Document 1: JP-A No. H5-52666
Patent Document 2: JP-A No. 2004-117145

SUMMARY OF INVENTION

Technical Problem

However, in thermosensitive recording materials or thermosensitive sheets that are conventionally used, due to their high sensitivity, the recording materials or sheets have low color development initiation temperatures, and are incapable of measuring high temperatures. Furthermore, since the color development characteristics against temperature changes are precipitous, and the color development density rapidly increases in a narrow temperature range, it is difficult to measure a thermal distribution over a small temperature difference or a wide temperature range.

Furthermore, there are also known thermal distribution measuring films that develop black color under the action of heat as described above; however, since the films can display only a single color, or have excessively high sensitivity to temperature changes, the temperature width of the thermal distribution that can be subjected to color display is narrow. Therefore, there is a problem that there are limitations on the applications to be measured that can be measured.

The invention was achieved in view of such circumstances as described above, and an object of the invention is to provide a thermal distribution display that has a wide temperature range in which the thermal distribution can be visualized, and is used for the measurement of a thermal distribution over a wide temperature range. Thus, the present invention is intended to achieve this object.

Means for Solving the Problems

Specific means for achieving the above-described object are as follows.

<1> It is a thermal distribution display including, on a support, a thermal distribution display layer that contains: at least two electron-donating dye precursors that develop mutually different color tones, the dye precursors including at least one electron-donating dye precursor that decomposes in a temperature range of 190° C. or higher to undergo a change in hue; at least one electron-accepting compound that allows the at least two electron-donating dye precursors to develop colors; and a binder, wherein, in the thermal distribution display layer, a temperature $T_{0.2}$, at which a density is 0.2 greater than a background density, satisfies the following formula (1):

$$\frac{0.2}{T_{0.2} - T_{min}} \leq 0.02 \qquad \text{Formula (1)}$$

In formula (1), $T_{0.2}$ represents a temperature [° C.] at which the density is 0.2 greater than a background density ($D_{min}$); and $T_{min}$ represents a color development initiation temperature [° C.].

<2> It is the thermal distribution display described in the above item <1>, in which the at least two electron-donating dye precursors are respectively encapsulated in microcapsules formed from wall materials having mutually different glass transition temperatures.

<3> It is the thermal distribution display described in the above item <1> or <2>, in which the at least one electron-donating dye precursor that decomposes in a temperature range of 190° C. or higher to undergo a change in hue is an indolylazaphthalide compound represented by the following formula (a):

Formula (a)

In formula (a), each of $R^1$, $R^2$, $R^3$, $R^4$ and $R^5$ independently represents a hydrogen atom, an alkyl group, a cycloalkyl group, an aralkyl group, an aryl group, a carbamoyl group, an alkoxy group, or a heterocyclic group.

<4> It is the thermal distribution display described in any one of the above items <1> to <3>, in which the at least one electron-accepting compound is a compound represented by the following formula (b):

Formula (b)

In formula (b), each of $R^1$, $R^2$, $R^3$ and $R^4$ independently represents a hydrogen atom, a halogen atom, an amino group, a carboxyl group, a carbamoyl group, a hydroxyl group, an alkylsulfonyl group, an alkyl group, or an aryl group, while any adjacent two of $R^1$ to $R^4$ may be bonded to each other and form a cyclic structure; M represents an n-valent metal atom; and n represents an integer from 1 to 3.

<5> It is the thermal distribution display described in any one of the above items <1> to <4>, in which the microcapsules have walls of a polymer having at least one of a urethane bond or a urea bond.

<6> It is the thermal distribution display described in any one of the above items <3> to <5>, which includes, as the at least two electron-donating dye precursors, the indolylazaphthalide compound represented by formula (a) that develops cyan color, and an electron-donating dye precursor that develops magenta color.

<7> It is the thermal distribution display described in the above item <6>, wherein a mass content ratio of the indolylazaphthalide compound represented by formula (a) that develops cyan color and the electron-donating dye precursor that develops magenta color is from 1/2 to 2/1.

<8> It is the thermal distribution display described in the above item <6> or <7>, in which the cyan color-developing indolylazaphthalide compound and the magenta color-developing electron-donating dye precursor are respectively encapsulated in microcapsules formed from wall materials having glass transition temperatures that are mutually different and that are lower than 220° C.

<9> The thermal distribution display described in any one of the above items <1> to <8>, including a light reflective layer on the thermal distribution display layer provided on the support.

Advantageous Effects of Invention

According to the invention, there is provided a thermal distribution display that has a wide temperature range in which the thermal distribution can be visualized, and is used for the measurement of a thermal distribution over a wide temperature range.

DESCRIPTION OF EMBODIMENTS

Hereinafter, the thermal distribution display of the invention will be described in detail.

The thermal distribution display of the invention is configured to include at least a support and a thermal distribution display layer that is disposed on the support, and the thermal distribution display layer on the support according to the invention is constructed at least including, as electron-donating dye precursors that develop mutually different color tones, two or more electron-donating dye precursors including an electron-donating dye precursor that decomposes in a temperature range of 190° C. or higher to undergo a change in hue; an electron-accepting compound which allows the electron-donating dye precursors to develop colors; and a binder. Furthermore, the thermal distribution display layer may also be constructed using other components such as a fluorescent brightening agent and a crosslinking agent, if necessary.

Furthermore, the thermal distribution display layer according to the invention is configured such that a temperature $T_{0.2}$, at which a density is 0.2 greater than a background density, satisfies the following formula (1).

Here, the background density refers to the optical density of a thermal distribution display layer having no recorded image (non-color-developed area) (that is, minimum density of the thermal distribution display layer ($D_{min}$)), which is obtainable before the thermal distribution display layer is subjected to a treatment of applying thermal energy from the outside, such as heating or warming.

Furthermore, $T_{0.2}$ is a temperature at which the optical density measured with a Macbeth densitometer (RD-918 type, manufactured by GretagMacbeth AG) by bringing a heat source heated to an arbitrary temperature into contact for 10 seconds at an applied pressure of 500 g/cm² using a ten serial type thermal characteristics testing machine (manufactured by Shinto Scientific Co., Ltd.), reaches [optical density of non-color-developed area+0.2].

$$\frac{0.2}{T_{0.2} - T_{min}} \leq 0.02 \qquad \text{Formula (1)}$$

In formula (1), $T_{0.2}$ represents a temperature [° C.] at which the density is 0.2 greater than a background density ($D_{min}$); and $T_{min}$ represents a color development initiation temperature [° C.].

That is, it is implied that the thermal distribution display layer according to the invention exhibits color development characteristics of low color development sensitivity (gradient of density increase against temperature increase), in which the temperature difference between the time point of color development initiation and the time point at which the density increases by 0.2 is 10° C. or more. This indicates that the thermal distribution display layer of the invention is distinguished from a so-called thermosensitive recording material on which an image is recorded using the heat of a heat emitting element such as a thermal head, or a laser. As disclosed in formula (1), when "$0.2/(T_{0.2}-T_{min})$" is greater than 0.02, the sensitivity is so high that a steep density change is exhibited even with a small temperature change, and the thermal distribution cannot be faithfully reproduced. In other words, when the formula (1) is satisfied, the color development density (optical density) of a color-developed area in which a color is developed by heating, undergoes a small change for a small temperature difference, and therefore, differences in the color development density can be exhibited over a wide temperature range. From the viewpoint that a thermal distribution display which exhibits a smaller temperature difference is enabled, the value of "$0.2/(T_{0.2}-T_{min})$" is more preferably 0.015 or less.

Meanwhile, $T_{0.2}$ is a temperature at the surface of the thermal distribution display layer, and is a value obtainable by measuring the temperature of the relevant surface. Also, $T_{min}$ is a temperature at which the density starts to increase from $D_{min}$, and is a value obtainable by measuring the density of a heated area using a Macbeth densitometer (RD-918, manufactured by GretagMacbeth AG).

Thermal distribution displays containing an electron-donating dye precursor together with an electron-accepting compound have been conventionally known; however, since the temperature range over which the thermal distribution can be measured is limited to a narrow range, thermal distribution displays applicable to various measurement temperatures have been required under the demand for measuring various temperature distributions.

Under such circumstances, in this invention, plural electron-donating dye precursors are incorporated into a thermal distribution display layer having the color development characteristics represented by formula (1), such that there exists at least one kind of an electron-donating dye precursor which "decomposes in a temperature range of 190° C. or higher to undergo a change in hue". The electron-donating dye precursor that decomposes in a temperature range of 190° C. or higher to undergo a change in hue is such that when the temperature reaches 190° C. or higher, the dye precursor itself decomposes and exhibits a color different from the color that is developed by a reaction with an electron-accepting compound. Thereby, along with an increase in temperature, the temperature range in which shades of a color or a change in hue occurs is extended to higher temperature regions, and changes in hue corresponding to a thermal distribution are exhibited over a wide temperature range including a higher temperature region of 190° C. or higher. As a result, even in a case in which there are relatively large temperature differences on the surface to be measured where it is intended to measure a thermal distribution, an image with visible gradations can be obtained, and the thermal distribution of the surface to be measured over a wide temperature range can be easily understood.

Figure 2:
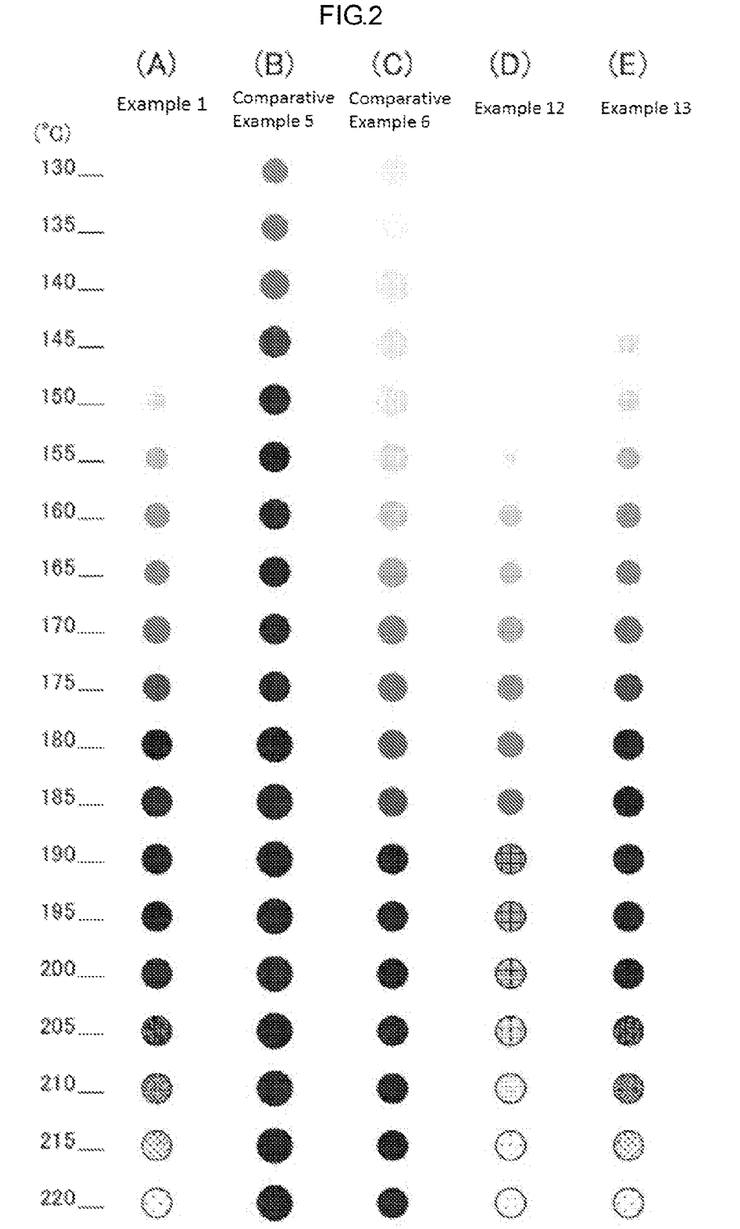
FIG. 2 is a thermal distribution diagram, in which column A is a thermal distribution diagram shown by the thermal distribution display material of Example 1; column B is a thermal distribution diagram shown by a thermal distribution display material of Comparative Example 5; column C is a thermal distribution diagram shown by the thermal distribution display material of Comparative Example 5; column D is a thermal distribution diagram shown by a thermal distribution display material of Example 12; and column E is a thermal distribution diagram shown by a thermal distribution display material of Example 13.

Specifically, as illustrated in column A, column D, and column E of FIG. 2, shades of a color and a change in hue are obtained in a wide temperature range including a higher temperature region of higher than 200° C. When it is intended to measure a temperature distribution of a wide range, in the materials that are conventionally used, as shown in column B and column C of FIG. 2, the temperature range in which shades of a color or changes in hue occur and the temperature range in which a thermal distribution is exhibited is narrow, and several kinds may be required. However, in the thermal distribution display of the invention, since color changes representing a thermal distribution are exhibited as continuous gradations in a wide temperature range, the required temperature range can be covered with only one kind.

<Thermal Distribution Display Layer>

The thermal distribution display of the invention is configured to include at least one thermal distribution display layer on a support. This thermal distribution display layer contains electron-donating dye precursors, an electron water-soluble compound, and a polymer.

The electron-donating dye precursors may be used in a form obtainable by mixing with a polymer, or may be used in a form of being encapsulated in microcapsules (hereinafter, may be simply called "capsules") that are formed using a polymer. When the electron-donating dye precursors are incorporated into the thermal distribution display layer together with a binder, thermoresponsiveness can be imparted, and also, the electron-donating dye precursors can be prevented from reacting with the electron-accepting compound and developing colors before thermal energy from the outside, such as heating or warming, is applied. Furthermore, storage stability of the thermal distribution display is also enhanced.

—Electron-Donating Dye Precursor—

The thermal distribution display layer according to the invention contains at least two electron-donating dye precursors (hereinafter, also simply referred to as "dye precursors"), and includes, as at least one of them, an electron-donating dye precursor which decomposes in a temperature range of 190° C. or higher to undergo a change in hue.

Electron-donating dye precursors have properties of developing colors by donating electrons or accepting protons of acids or the like, and can include substantially colorless precursors without any limitations. Among them, particularly, a colorless compound having a partial skeleton of a lactone, a lactam, a sultone, a spiropyran, an ester, an amide or the like, in which such a partial skeleton is subjected to ring-opening or cleavage when the compound is brought into contact with an electron-accepting compound, is preferred.

Examples of the electron-donating dye precursors include triphenylmethanephthalide-based compounds, fluoran-based compounds, phenothiazine-based compounds, indolylphthalide-based compounds, leuco auramine-based compounds, rhodamine lactam-based compounds, triphenylmethane-based compounds, triazene-based compounds, spiropyran-based compounds, fluorene-based compounds, pyridine-based compounds, and pyrazine-based compounds.

Specific examples of the phthalides include the compounds described in Reissue U.S. Pat. No. 23,024, and U.S. Pat. Nos. 3,491,111, 3,491,112, 3,491,116, and 3,509,174.

Specific examples of the fluorans include the compounds described in U.S. Pat. Nos. 3,624,107, 3,627,787, 3,641,011, 3,462,828, 3,681,390, 3,920,510, and 3,959,571.

Specific examples of the spiropyrans include the compounds described in U.S. Pat. No. 3,971,808.

Specific examples of the pyridine-based and pyrazine-based compounds include the compounds described in U.S. Pat. Nos. 3,775,424, 3,853,869, and 4,246,318.

Specific examples of the fluorene-based compounds include the compounds described in JP-A No. S63-094878.

Specific examples include 2-anilino-3-methyl-6-diethylaminofluoran, 2-anilino-3-methyl-6-N-cyclohexyl-N-methylaminofluoran, 2-p-chloroanilino-3-methyl-6-dibutylaminofluoran, 2-anilino-3-methyl-6-dioctylaminofluoran, 2-anilino-3-chloro-6-diethylaminofluoran, 2-anilino-3-methyl-6-N-ethyl-N-isoamylaminofluoran, 2-anilino-3-methyl-6-N-ethyl-N-dodecylaminofluoran, 2-anilino-3-methoxy-6-dibutylaminofluoran, 2-o-chloroanilino-6-dibutylaminofluoran, 2-p-chloroanilino-3-ethyl-6-N-ethyl-N-isoamylaminofluoran, 2-o-chloroanilino-6-p-butylanilinofluoran, 2-anilino-3-pentadecyl-6-diethylaminofluoran, 2-anilino-3-ethyl-6-dibutylaminofluoran, 2-o-toluidino-3-methyl-6-diisopropylaminofluoran, 2-anilino-3-methyl-6-N-isobutyl-N-ethylaminofluoran, 2-anilino-3-methyl-6-N-ethyl-N-tetrahydrofurfurylaminofluoran, 2-anilino-3-chloro-6-N-ethyl-N-isoamylaminofluoran, 2-anilino-3-methyl-6-N-methyl-N-y-ethoxypropylaminofluoran, 2-anilino-3-methyl-6-N-ethyl-N-y-ethoxypropylaminofluoran, and 2-anilino-3-methyl-6-N-ethyl-N-y-propoxypropylaminofluoran.

Furthermore, for at least one of the electron-donating dye precursors, an electron-donating dye precursor which decomposes in a temperature range of 190° C. or higher to undergo a change in hue is used. This dye precursor develops a color, at a temperature of lower than 190° C., by a reaction with an electron-accepting compound and exhibits a prescribed hue (for example, cyan color), and at a temperature of 190° C. or higher, the dye precursor thermally decomposes per se and exhibits a color different from the foregoing prescribed hue (for example, yellow color). When such a dye precursor is incorporated together with another dye precursor that develops a color different from this color, a thermal distribution in a high temperature range where display has been conventionally difficult, comes to be displayed.

The "electron-donating dye precursor which decomposes in a temperature range of 190° C. or higher to undergo a change in hue" can be selected without any limitations from dye precursors which exhibit, when decomposed in a temperature range of 190° C. or higher, a hue different from the hue exhibited by a reaction with an electron-accepting compound, and bring a change in hue. Such a dye precursor is preferably an indolylazaphthalide compound (4-azaphthalide-based compound) represented by the following formula (a).

Formula (a)

In formula (a), each of $R^1$, $R^2$, $R^3$, $R^4$ and $R^5$ independently represents a hydrogen atom, an alkyl group, a cycloalkyl group, an aralkyl group, an aryl group, a carbamoyl group, an alkoxy group, or a heterocyclic group.

The alkyl group represented by $R^1$ to $R^5$ may be unsubstituted or may be substituted, and the alkyl group is preferably an alkyl group having 1 to 12 carbon atoms. Examples thereof include a methyl group, an ethyl group, a propyl group, a t-butyl group, an isopropyl group, an octyl group, and a 2-ethylhexyl group.

The cycloalkyl group represented by $R^1$ to $R^5$ may be unsubstituted or may be substituted, and the cycloalkyl group is preferably a cycloalkyl group having 3 to 8 carbon atoms. Examples thereof include a cyclopropyl group, and a cyclohexyl group.

The aralkyl group represented by $R^1$ to $R^5$ may be unsubstituted or may be substituted, and the aralkyl group is preferably an aralkyl group having 7 to 20 carbon atoms. Examples thereof include a benzyl group and a phenethyl group.

The aryl group represented by $R^1$ to $R^5$ may be unsubstituted or may be substituted, and the aryl group is preferably an aryl group having 6 to 10 carbon atoms. Examples thereof include a phenyl group and a naphthyl group.

The carbamoyl group represented by $R^1$ to $R^5$ may be unsubstituted or may be substituted, and the carbamoyl group is preferably a carbamoyl group having 1 to 8 carbon atoms. Examples thereof include an unsubstituted carbamoyl group, a methylcarbamoyl group, an ethylcarbamoyl group, and a dimethylcarbamoyl group.

The alkoxy group represented by $R^1$ to $R^5$ may be unsubstituted or may be substituted, and the alkoxy group is preferably an alkoxy group having 1 to 8 carbon atoms. Examples thereof include a methoxy group, an ethoxy group, a propoxy group, a 2-propoxy group, and a t-butoxy group.

The heterocyclic group represented by $R^1$ to $R^5$ may be unsubstituted or may be substituted, and the heterocyclic group is preferably a heterocyclic group having 5 to 10 carbon atoms and containing a nitrogen atom, an oxygen atom, or a sulfur atom as a heteroatom. Examples of the heterocyclic group include tetrahydrofuryl, pyrrolidinyl, pyrazolidinyl, imidazolidinyl, piperidyl, morpholinyl, thiamorpholinyl, and piperazinyl.

Examples of the indolylazaphthalide compound represented by formula (a) include compounds shown below. However, in this invention, the compounds are not intended to be limited to these.

| | $R^1$ | $R^2$ | $R^3$ | $R^4$ | $R^5$ |
|---|---|---|---|---|---|
| 1 | $C_2H_5$ | $C_2H_5$ | $CH_3$ | $CH_3$ | $C_2H_5$ |
| 2 | $C_3H_7$ | $C_3H_7$ | $NHCOCH_3$ | $CH_3$ | $C_8H_{17}$ |
| 3 | $C_2H_5$ | $C_2H_5$ | $OC_2H_5$ | $CH_3$ | $C_8H_{17}$ |
| 4 | $C_2H_5$ | $C_2H_5$ | $OC_2H_5$ | $CH_3$ | $C_2H_5$ |
| 5 | $C_3H_7$ | $C_3H_7$ | $NHCOC_2H_5$ | $CH_3$ | $C_6H_{13}$ |
| 6 | $CH_3$ | $CH_3$ | $OCH_3$ | $CH_3$ | $C_2H_5$ |
| 7 | $C_3H_7$ | $C_3H_7$ | $NHCOCH_3$ | $CH_3$ | $C_4H_9$ |

-continued

| | R¹ | R² | R³ | R⁴ | R⁵ |
|---|---|---|---|---|---|
| 8 | C₃H₇ | C₃H₇ | NHCOC₃H₇ | CH₃ | C₄H₉ |
| 9 | C₆H₅ | C₆H₅ | CH₃ | CH₃ | C₂H₅ |
| 10 | C₆H₅ | CH₃ | CH₃ | CH₃ | C₂H₅ |
| 11 | Cyclohexyl | Cyclohexyl | CH₃ | CH₃ | C₄H₉ |
| 12 | C₂H₅ | C₂H₅ | CH₃ | CH₃ | CH₂C₆H₅ |
| 13 | C₂H₅ | C₂H₅ | Pyrrolidinyl | CH₃ | C₄H₉ |

The thermal distribution display layer according to the invention preferably contains two or more kinds including at least one indolylazaphthalide compound represented by formula (a) as the "electron-donating dye precursor which decomposes in a temperature range of 190° C. or higher to undergo a change in hue", and at least one other dye precursor.

Furthermore, from the viewpoint that a satisfactory thermal distribution display is displayed over a wide temperature range, an embodiment in which two or more kinds including at least one cyan color-developing indolylazaphthalide compound represented by formula (a) and at least one magenta color-developing electron-donating dye precursor are included, is preferred. Furthermore, among others, more preferred is an embodiment in which the at least one magenta color-developing electron-donating dye precursor (and preferably, at least one cyan color-developing indolylazaphthalide compound represented by formula (a)) is encapsulated in microcapsules that have a Tg of <220° C.

In this case, there are no particular limitations on the content ratio of the cyan color-developing indolylazaphthalide compound and the magenta color-developing electron-donating dye precursor (cyan/magenta ratio [mass ratio]), but when the content ratio is 1/2 to 2/1, it is preferable from the viewpoint that satisfactory display of a thermal distribution is obtained in a wide temperature range.

A content ratio of each of the plural electron-donating dye precursors (including the "electron-donating dye precursor which decomposes in a temperature range of 190° C. or higher to undergo a change in hue") that are included in the thermal distribution display layer is preferably 10% by mass to 100% by mass, and more preferably 20% by mass to 60% by mass, relative to the electron-accepting compound. When a content ratio of each of the electron-donating dye precursors is 10% by mass or more, a developed color density that can be visualized is easily obtained. Furthermore, when a content ratio of the electron-donating dye precursors is 100% by mass or less, it is advantageous in that satisfactory storage stability is maintained, and an increase in the background density is suppressed to a low level.

Also, the total amount of the electron-donating dye precursors in the thermal distribution display layer is preferably 8% by mass to 30% by mass relative to the total mass of the layer, from the viewpoint of the developed color density that can be visualized.

The electron-donating dye precursor is preferably used as an organic polymer complex encapsulated in capsules produced from a polymer that will be described below, from the viewpoints of storage stability and prevention of an increase in the background density.

Furthermore, the thermal distribution display layer contains two or more kinds of electron-donating dye precursors, but it is preferable that the electron-donating dye precursors be respectively encapsulated in microcapsules formed from wall materials having mutually different glass transition temperatures (Tg). At this time, the temperature difference between the Tg's of the microcapsules having different Tg's is preferably 15° C. or more, more preferably in the range of from 15° C. to 40° C., and even more preferably in the range of from 20° C. to 30° C., from the viewpoint of having a satisfactory thermal distribution display over a wide temperature range.

—Polymer—

The electron-donating dye precursors contained in the thermal distribution display layer may be incorporated together with a polymer. For example, when the electron-donating dye precursors are used in the form of the organic polymer complex, the electron-donating dye precursors may be encapsulated in capsules produced from polymers.

The polymer can be selected without any particular limitations from polymer compounds that are capable of forming organic polymer complexes together with the electron-donating dye precursors, and examples thereof include polyethylene, polystyrene, polyvinyl, polyurethane, polyurea, and polyurethane/polyurea. Among them, it is preferable that from the viewpoints of storage stability and prevention of an increase in the background density, the electron-donating dye precursors be incorporated as dye precursor-containing microcapsules (organic polymer complexes) in which the electron-donating dye precursors are encapsulated in microcapsules produced from a polymer obtainable by using an isocyanate compound that will be described below and a volatile organic solvent, and it is more preferable that the electron-donating dye precursors be incorporated particularly as dye precursor-containing microcapsules having walls of a polymer having a urethane bond and/or a urea bond. Among others, the polymer having a urethane bond and/or a urea bond is particularly preferably polyurethane/polyurea.

(Isocyanate Compound)

An isocyanate compound intended for obtaining the polymer includes the case of an isocyanate compound having two or more isocyanate groups in an aromatic compound, a hydrocarbon compound or the like, as well as the case of a condensate, a polymer, an addition product or the like obtained using an isocyanate compound. A compound having two or more isocyanate groups in one molecule (including a polymer, an adduct or the like) is preferred.

Examples of the compound having two isocyanate groups in an aromatic compound, a hydrocarbon compound or the like include m-phenylene diisocyanate, p-phenylene diisocyanate, 2,6-tolylene diisocyanate, 2,4-tolylene diisocyanate, naphthalene-1,4-diisocyanate, diphenylmethane-4,4'-diisocyanate, 3,3'-dimethoxybiphenyl diisocyanate, 3,3'-dimethyldiphenylmethane-4,4'-diisocyanate, xylylene-1,4-diisocyanate, xylylene-1,3-diisocyanate, 4-chloroxylylene-1,3-diisocyanate, 2-methylxylylene-1,3-diisocyanate, 4,4'-diphenylpropane diisocyanate, 4,4'-diphenylhexafluoropropane diisocyanate, trimethylene diisocyanate, hexamethylene diisocyanate, propylene-1,2-diisocyanate, butylene-1,2-diisocyanate, cyclohexylene-1,2-diisocyanate, cyclohexylene-1,3-diisocyanate, cyclohexylene-1,4-diisocyanate, dicyclohexylmethane-4,4'- diisocyanate, 1,4-bis(isocyanatomethyl)cyclohexane, 1,3-bis(isocyanatomethyl)cyclohexane, isophorone diisocyanate, and lysine diisocyanate.

In the above, bifunctional diisocyanate compounds have been listed as examples, but trifunctional triisocyanate compounds and tetrafunctional tetraisocyanate compounds analogized form these may also be used.

Furthermore, adducts of the isocyanate compounds described above with bifunctional alcohols and phenols such as ethylene glycols and bisphenols can also be utilized.

Regarding examples of the condensate, polymer or addition product using an isocyanate compound, a biuret or an isocyanurate, which are trimers of the bifunctional isocyanate compounds described above; a polyfunctionalized addition product of a polyol such as trimethylolpropane and a bifunctional isocyanate compound; a formalin condensate of benzene isocyanate; a polymer of an isocyanate compound having a polymerizable group, such as methacryloyloxyethyl isocyanate; lysine triisocyanate, and the like can also be used. Particularly, products obtained by using xylene diisocyanate and a hydrogenation product thereof, hexamethylene diisocyanate, tolylene diisocyanate and a hydrogenation product thereof as main raw materials, and converting these compounds into trimers (biuret or isocyanurate) as well as polyfunctionalized adducts with trimethylolpropane, are preferred.

In regard to these compounds, the details are described in "Polyurethane Resin Handbook" (edited by Keiji IWATA, published by the Nikkan Kogyo Shimbun, Ltd. (1987)).

Among these, the polyfunctional isocyanate is preferably an aromatic polyfunctional isocyanate, and for example, 2,4-tolylene diisocyanate, 2,6-tolylene diisocyanate, xylylene-1,4-diisocyanate, xylylene-1,3-diisocyanate, and an adduct of trimethylolpropane and xylylene-1,4-diisocyanate or xylylene-1,3-diisocyanate are preferred; and particularly, xylylene-1,4-diisocyanate and xylylene-1,3-diisocyanate, and an adduct of trimethylolpropane and xylylene-1,4-diisocyanate or xylylene-1,3-diisocyanate are preferred.

(Volatile Organic Solvent)

The volatile organic solvent is an organic solvent having a boiling point of higher than or equal to 40° C. and lower than 150° C., and is preferably an organic solvent having a boiling point of from 40° C. to 130° C.

Examples of the volatile organic solvent used to obtain the above-described polymer include ethyl acetate (boiling point: 77° C.), isopropyl acetate (boiling point: 88° C.), butyl acetate (boiling point: 124° C. to 127° C.), isobutyl acetate (boiling point: 118° C.), methylene chloride (boiling point: 40° C.), and tetrahydrofuran (boiling point: 66° C.). These may also be used as mixtures of two or more kinds. Among these, ethyl acetate is particularly preferred.

—Production of Organic Polymer Complex—

The organic polymer complex can be produced by, for example, dispersing an electron-donating dye precursor-containing liquid containing the electron-donating dye precursors, the isocyanate compound and the volatile organic solvent described above in an aqueous phase to thereby prepare a dispersion liquid in which oil droplets containing the electron-donating dye precursor-containing liquid are dispersed (dispersion process); and subjecting the isocyanate compound in the oil droplets to a polymerization reaction (polymerization process).

The content of the volatile organic solvent in the dispersion liquid when the reactivity of the isocyanate compound in the polymerization process is 70%, is preferably adjusted to 10% or less relative to the content at the time of initiation of the polymerization reaction.

Hereinafter, the method for producing an organic polymer complex will be described in detail.

<<Dispersion Process>>

The dispersion process according to the invention is a process of emulsifying and dispersing the electron-donating dye precursor-containing liquid (oil phase) as oil droplets in an aqueous phase. Emulsifying dispersion can be easily carried out using those means conventionally used in fine particle emulsification, such as a high speed stirrer and an ultrasonic dispersing apparatus, for example, a homogenizer, a Manton Gaulin, an ultrasonic dispersing machine, a dissolver, a KD mill, and other known emulsifying dispersion apparatuses.

The mixing ratio of the oil phase with respect to the aqueous phase (oil phase mass/aqueous phase mass) is preferably 0.5 to 1.5, and more preferably 0.7 to 1.2. When the mixing ratio is in the range of 0.5 to 1.5, the emulsion liquid can maintain an appropriate viscosity, has excellent production suitability, and has excellent stability of the emulsion liquid.

For the aqueous phase used, it is preferable to use an aqueous solution having a water-soluble polymer dissolved therein, as a protective colloid. The water-soluble polymer allows dispersion to be achieved uniformly and easily, and also works as a dispersion medium that stabilizes the emulsified and dispersed aqueous solution.

Examples of the water-soluble polymer include polyvinyl alcohol and modification products thereof, polyacrylic acid amide and derivatives thereof, an ethylene/vinyl acetate copolymer, a styrene/maleic anhydride copolymer, an ethylene/maleic anhydride copolymer, an isobutylene/maleic anhydride copolymer, polyvinylpyrrolidone, an ethylene/acrylic acid copolymer, a vinyl acetate/acrylic acid copolymer, carboxymethyl cellulose, methyl cellulose, casein, gelatin, starch derivatives, gum arabic, and sodium alginate. Polyvinyl alcohol and modification products thereof, gelatin and modification products thereof, and cellulose derivatives are preferably used.

It is preferable that these water-soluble polymers do not react with isocyanate compounds or react only with extreme difficulties, and for example, a water-soluble polymer having reactive amino groups in the molecular chain as in the case of gelatin, it is important to have reactivity eliminated in advance.

The water-soluble polymers may be used singly, or two or more kinds may be used in combination.

In the invention, since polyether works also as a surfactant, when a polyether compound is added to the electron-donating dye precursor-containing liquid, dispersion can be carried out stably without separately adding a surfactant. However, if necessary, a surfactant may also be added thereto to the extent that the performance of the thermal distribution display is not adversely affected. The surfactant may be used by being added to any of the oil phase or the aqueous phase. The amount of use of the surfactant is preferably 1% by mass or less, and particularly 0.5% by mass or less, relative to the mass of the oil phase.

The Surfactants Used for Emulsifying Dispersion are Described in Paragraphs [0066] to of JP-A No. 2010-180294, and the surfactants can be appropriately applied to the thermal distribution display of the invention.

The particle size of the emulsion particles, which are oil droplets obtained by the dispersion process, is preferably the same particle size as the volume average 50% particle size (D50v) of the organic polymer complex described above, and the same also applies to the preferred range of the particle size of the emulsion particles.

<<Polymerization Process>>

The polymerization process is a process of subjecting the isocyanate compound contained in oil droplets to a polymerization reaction. The content of a volatile organic solvent in the dispersion liquid can be appropriately adjusted by regulating the stirring speed or stirring time for the dispersion liquid, and the liquid temperature or exhaust air volume at the time of the polymerization reaction. The polymerization reaction can be carried out by adding a polymerization reaction catalyst for the isocyanate compound into the dispersion liquid, or by increasing the temperature of the dispersion liquid.

In a conventional method for producing microcapsules, a compound which causes an addition reaction with an isocyanate compound, for example, a polyol or a polyfunctional amino compound, is added to the aqueous phase, and the isocyanate contained in the oil phase is subjected to an addition reaction at the interface with active hydrogen of water molecules as well as the polyol or polyfunctional amino compound contained in the aqueous phase. Thus, a polyurethane or a polyurea is produced, and thus walls are formed.

Specific examples of the polyol that can be added to the aqueous phase include propylene glycol, glycerin and trimethylolpropane, and only one kind may be used, or two or more kinds may be used in combination. Furthermore, examples of the polyfunctional amino compound that can be added to the aqueous phase include diethylenetriamine and tetraethylenepentamine, and only one kind may be used, or two or more kinds may be used in combination. Furthermore, a polyol and a polyfunctional amino compound may be used in combination. These compounds are also described in "Polyurethane Resin Handbook" described above.

In order to prevent aggregation of organic polymer complexes such as microcapsules during the polymerization process, it is preferable to decrease the probability of collision between the organic polymer complexes by adding water, and it is also preferable to sufficiently perform stirring. The amount of addition of water is preferably adjusted such that the concentration of the electron-donating dye precursor-containing liquid reaches 2% by mass to 50% by mass, and more preferably 5% by mass to 30% by mass.

Also, a dispersant for aggregation prevention may be further added during the polymerization process. Along with the progress of the polymerization reaction, generation of carbon dioxide gas is observed, and the end of the generation can be considered as an approximate end point of the forming reaction. Usually, an intended organic polymer complex can be obtained by allowing the system to react for several hours.

In the method for producing the organic polymer complex described above, if necessary, a metal-containing dye, a charge controlling agent such as nigrosin, or any other additive substances can be added. These additives can be incorporated at the time of wall formation, or at any arbitrary time point.

After the polymerization process, it is also preferable to heat the system in order to remove the volatile organic solvent that is contained in the organic polymer composite. If the volatile organic solvent remains, the solvent slowly volatilizes during storage, and the performance may easily become unstable. The heating temperature for removing the volatile organic solvent may vary depending on the kind of the volatile organic solvent used, but the heating temperature is preferably lower than 100° C., and more preferably 40° C. to 70° C.

A content of the electron-donating dye precursor in the electron-donating dye precursor-containing liquid is preferably 5% by mass to 50% by mass, and more preferably 10% by mass to 30% by mass.

A content of the isocyanate compound in the electron-donating dye precursor-containing liquid is preferably 2% by mass to 50% by mass, and more preferably 5% by mass to 30% by mass.

Furthermore, a content of the isocyanate compound in the electron-donating dye precursor-containing liquid is preferably 5 parts by mass to 75 parts by mass, and more preferably 10 parts by mass to 50 parts by mass, relative to 100 parts by mass of the volatile organic solvent. When the content of the isocyanate compound is 5 parts by mass to 75 parts by mass relative to 100 parts by mass of the volatile organic solvent, it is easy to control the reactivity of the isocyanate compound by the control of evaporation of the volatile organic solvent.

A content of the volatile organic solvent in the electron-donating dye precursor-containing liquid is 20% by mass to 90% by mass, and more preferably 30% by mass to 70% by mass.

The electron-donating dye precursor-containing liquid may appropriately contain an ultraviolet absorber, an oxidation preventing agent and the like as necessary.

The electron-donating dye precursor-containing liquid is prepared by mixing a intended amount of electron-donating dye precursors, an isocyanate compound, a volatile organic solvent, and other components that are optionally used, using a known technique such as stirring or dispersing. The electron-donating dye precursor-containing liquid may be in a solution state or may be in a dispersion liquid state.

—Electron-Accepting Compound—

The thermal distribution display layer according to the invention contains at least one electron-accepting compound that causes the electron-donating dye precursor to develop color. When the electron-donating dye precursor is used as an organic polymer complex by mixing with a polymer or by encapsulating, it is preferable for the electron-accepting compound not to be included in the organic polymer complex.

Examples of the electron-accepting compound include phenolic derivatives, salicylic acid derivatives, and hydroxybenzoic acid esters. Among these, particularly, bisphenols and hydroxybenzoic acid esters are preferred. Examples include 2,2-bis(p-hydroxyphenyl)propane(bisphenol A), 2,2-bis(p-hydroxyphenyl)pentane, 2,2-bis(p-hydroxyphenyl)ethane, 2,2-bis(p-hydroxyphenyl)butane, 2,2-bis(4'-hydroxy-3',5'-dichlorophenyl)propane, 1,1-(p-hydroxyphenyl)cyclohexane, 1,1-(p-hydroxyphenyl)propane, 1,1-(p-hydroxyphenyl)pentane, 1,1-(p-hydroxyphenyl)-2-ethylhexane, 3,5-di($\alpha$-methylbenzyl)salicylic acid and polyvalent metal salts thereof, 3,5-di(tert-butyl)salicylic acid and polyvalent metal salts thereof, 3-$\alpha,\alpha$-dimethylbenzyl-salicylic acid and polyvalent metal salts thereof, butyl p-hydroxybenzoate, benzyl p-hydroxybenzoate, 2-ethylhexyl p-hydroxybenzoate, p-phenylphenol, and p-cumylphenol.

Among the electron-accepting compounds, a compound represented by the following formula (b) is preferred. This compound has an advantage that when the electron-donating dye precursors are incorporated as organic polymer complexes by encapsulating the dye precursors in microcapsules, for example, the effect of decreasing the Tg of capsule walls is small, and in a thermal distribution display layer which satisfies the above formula (1), since the developed color density exhibits a small change against a small temperature difference, a difference in the developed color density can be displayed for various temperatures.

Formula (b)

In formula (b), each of $R^1$, $R^2$, $R^3$ and $R^4$ independently represents a hydrogen atom, a halogen atom, an amino group, a carboxyl group, a carbamoyl group, a hydroxyl group, an alkylsulfonyl group, an alkyl group, or an aryl group, while any adjacent two of $R^1$ to $R^4$ may be bonded to each other and form a cyclic structure. M represents an n-valent metal atom, n represents an integer from 1 to 3.

In formula (b), the alkyl group represented by $R^1$, $R^2$, $R^3$ or $R^4$ may be unsubstituted or may be substituted, and preferably has 1 to 8 carbon atoms. The alkyl group may be linear, branched, or cyclic, and may further have a substituent such as a phenyl group or a halogen atom.

Examples of the alkyl group represented by $R^1$, $R^2$, $R^3$ or $R^4$ include methyl, ethyl, t-butyl, cyclohexyl, and 2-phenylethyl groups. The alkyl group more preferably has a linear or branched structure and contains 1 to 4 carbon atoms (not including the number of carbon atoms of the substituent).

The aryl group represented by $R^1$, $R^2$, $R^3$ or $R^4$ may be unsubstituted or may be substituted, and is preferably an aryl group with a 3-membered to 6-membered ring and 3 to 6 carbon atoms, which may have a heteroatom.

Examples of the aryl group represented by $R^1$, $R^2$, $R^3$ or $R^4$ include phenyl, benzyl, tolyl, naphthyl, 2-furyl, 2-thienyl, and 2-pyridyl. The aryl group represented by $R^1$, $R^2$, $R^3$ or $R^4$ is more preferably a 5-membered or 6-membered aryl group having 6 to 8 carbon atoms without any heteroatom.

Examples of the halogen atom represented by $R^1$, $R^2$, $R^3$ or $R^4$ include a chlorine atom, a bromine atom, and an iodine atom.

Examples of the substituent that can further have an amino group, a carbamoyl group, an alkyl group and an aryl group, include a halogen atom, an amino group, a carboxyl group, a carbamoyl group, a hydroxyl group, an alkylsulfonyl group, an alkyl group, and an aryl group, while the number of carbon atoms of the substituent is preferably 1 to 8.

Among those described above, $R^1$ to $R^4$ each preferably represent a hydrogen atom, an alkyl group, or an aryl group.

Regarding a preferred combination of $R^1$ to $R^4$, an embodiment in which $R^1$ is a hydrogen atom, $R^2$ is an alkyl group having 2 or 3 carbon atoms and having a phenyl group (if the number of carbon atoms of the phenyl group is included, the number of carbon atoms is 8 or 9), $R^3$ is a hydrogen atom, and $R^4$ is an alkyl group having 2 or 3 carbon atoms and having a phenyl group (if the number of carbon atoms of the phenyl group is included, the number of carbon atoms is 8 or 9), is preferred.

Furthermore, any adjacent two among $R^1$ to $R^4$ may be bonded to each other and form a ring.

M in formula (b) represents an n-valent metal atom, and n represents an integer from 1 to 3.

Examples of the M include a sodium atom, a potassium atom, a copper atom, an aluminum atom, a calcium atom, and a zinc atom. Among them, M is preferably a polyvalent metal atom, that is, a metal atom having a valency of 2 or higher, and M is preferably an aluminum atom, a calcium atom, or a zinc atom. More preferably, M is a zinc atom.

Specific examples of the compound represented by formula (b) will be shown below. However, in this invention, the examples are not intended to be limited to these.

Specific examples include zinc, aluminum, calcium and copper salts of 4-pentadecylsalicylic acid, 3,5-di(α-methylbenzyl)salicylic acid, 3,5-di(ter-octyl)salicylic acid, 5-α—(p-α-methylbenzylphenyl)ethylsalicylic acid, 3-α-methylbenzyl-5-ter-octylsalicylic acid, 5-tetradecylsalicylic acid, 4-hexyloxysalicylic acid, 4-cyclohexyloxysalicylic acid, 4-decyloxysalicylic acid, 4-dodecyloxysalicylic acid, 4-pentadecyloxysalicylic acid, and 4-octadecyloxysalicylic acid.

In this invention, these electron-accepting compounds may be used singly, or two or more kinds may be used in combination at any ratio.

A content of the electron-accepting compound is preferably 20% by mass to 1000% by mass, and more preferably 50% by mass to 500% by mass relative to the total mass of the electron-donating dye precursors, from the viewpoint of the developed color density.

—Binder—

The thermal distribution display layer according to the invention contains at least one binder.

Examples of the binder include polyvinyl alcohol, a modified polyvinyl alcohol, hydroxyethyl cellulose, hydroxypropyl cellulose, epichlorohydrin-modified polyamide, an ethylene-maleic anhydride copolymer, a styrene-maleic anhydride copolymer, an isobutylene-maleic anhydride-salicylic acid copolymer, polyacrylic acid, polyacrylic acid amide, methylol-modified polyacrylamide, a starch derivative, casein, and gelatin.

Furthermore, for the purpose of imparting water resistance to these binders, a water resistance improving agent may be added, or an emulsion of a hydrophobic polymer, specifically, an acrylic resin emulsion, a styrene-butadiene latex, or the like may be added.

A content of the binder is preferably 5% by mass to 30% by mass, and more preferably 10% by mass to 20% by mass, relative to the total solid content of the thermal distribution display layer, from the viewpoint of preventing transfer of the thermal distribution display layer to a heat source.

the binder used in the thermal distribution display layer is preferably polyvinyl alcohol (PVA) from the viewpoint of obtaining satisfactory transparency, and modified PVA's such as a carboxy-modified polyvinyl alcohol or an alkyl ether-modified polyvinyl alcohol can also be used.

—Other Components—

The thermal distribution display layer according to the invention may further contain other components, in addition to the electron-donating dye precursors, electron-accepting compound and binder.

The other components are not particularly limited, and can be appropriately selected according to the purpose or necessity. Examples of the other components include a crosslinking agent, a sensitizer, a pigment, a lubricating agent, a known thermally fusible material, an ultraviolet absorber, an oxidation inhibitor, and an antistatic agent.

Among the binders, in the case of using a water-soluble polymer compound (for example, gelatin or polyvinyl alcohol), storage stability can be further enhanced by incorporating a crosslinking agent and crosslinking the binder.

The crosslinking agent can be appropriately selected from known crosslinking agents. Examples thereof include water-soluble initial condensates such as N-methylolurea, N-methylolmelamine, and urea-formalin; dialdehyde compounds such as glyoxal and glutaraldehyde; inorganic crosslinking agents such as boric acid and borax; and polyamidoepichlorohydrin.

The thermal distribution display layer may contain a pigment. Regarding the pigment, an organic pigment and an inorganic pigment can both be used. The pigment used in the thermal distribution display layer is preferably such that the volume average particle size is 0.10 μm to 5.0 μm.

Furthermore, it is still acceptable to provide a light reflective layer containing a pigment that will be described below, on the thermal distribution display layer on a support, with or without the thermal distribution display layer containing a pigment at the same time.

Other components in addition to the crosslinking agent, specifically, a sensitizer, a pigment, a lubricating agent, a known thermally fusible material, an ultraviolet absorber, an oxidation inhibitor, an antistatic agent and the like, are described in paragraphs [0091] to of JP-A No. 2010-180294, and these components can be appropriately applied to the thermal distribution display of the invention.

—Formation of Thermal Distribution Display Layer—

The thermal distribution display layer according to the invention can be formed by applying, on a support, a coating liquid for thermal distribution display layer formation that has been prepared by blending electron-donating dye precursors (preferably, organic polymer complexes such as microcapsules encapsulating electron-donating dye precursors), an electron-accepting compound, a binder, and optionally, those other components which the thermal distribution display layer can contain.

In this invention, an electron-accepting compound may be added to the coating liquid for thermal distribution display layer formation, and a thermal sensitizer and the like may also be added. In this case, the respective components can be added after being separately subjected to emulsifying dispersion or solid dispersion and micronization, or can be added after being appropriately mixed, subsequently being subjected to emulsifying dispersion or solid dispersion, and micronization. Regarding the method for performing emulsifying dispersion, these compounds can be dissolved in an organic solvent, and an aqueous solution of a water-soluble polymer can be added thereto while the system is stirred with a homogenizer or the like. On the occasion of accelerating micronization, it is preferable to use a hydrophobic organic solvent, a surfactant, or a water-soluble polymer.

In order to solid disperse an electron-accepting compound, a thermal sensitizer and the like, a method of introducing these powders into an aqueous solution of a water-soluble polymer, and producing fine particles using a known dispersing means such as a ball mill, is suitable. On the occasion of micronization, it is preferable to carry out micronization so as to obtain a particle size which can satisfy the characteristics required in the thermal distribution display and a method for the production thereof, such as heat sensitivity, storability, transparency of the recording layer, and production suitability.

The electron-accepting compound is preferably prepared to be in a solid-dispersed state, not in an emulsified state.

The coating liquid for thermal distribution display layer formation can be prepared by, for example, mixing a solid dispersion containing the organic polymer complex produced as described above and the electron-accepting compound.

The water-soluble polymer used as a protective colloid at the time of production of the organic polymer complex such as microcapsules, and the water-soluble polymer used as a protective colloid at the time of production of the dispersion, function as binders in the thermal distribution display layer. Furthermore, it is a preferred embodiment to prepare a coating liquid for thermal distribution display layer formation by adding and mixing the binder separately from these protective colloids.

The thermal distribution display layer according to the invention is preferably provided on a support in an amount in the range of 1 $g/m^2$ to 25 $g/m^2$. Furthermore, the thickness of the thermal distribution display layer is preferably 1 μm to 25 μm.

The thermal distribution display layer can be used as a laminate of two or more layers as described above, and in this case, it is preferable that the content of all the thermal distribution display layers relative to the total mass of the thermal distribution display be 1 $g/m^2$ to 25 $g/m^2$.

<Support>

The thermal distribution display of the invention is configured to include a support.

The support can be appropriately selected from known supports. Regarding the examples of the support, use of a neutral paper, an acidic paper, a regenerated paper, a polyolefin resin-laminated paper, a synthetic paper, a polyester film, a polyimide film, a cellulose derivative film such as a cellulose triacetate film, a polystyrene film, a polyolefin film such as a polypropylene film or a polyethylene film; films formed from one kind or a mixture of two or more kinds of poly-4-methylpentene-1, an ionomer, polyvinyl chloride, polyvinylidene chloride, an ABS resin, an AS resin, a methacrylic resin, polyvinyl alcohol, EVA, an epoxy resin, an unsaturated polyester resin, a phenol resin, a urea/melamine resin, a polyurethane resin, a silicone resin, a polyamide resin, polyacetal, polycarbonate, modified polyphenylene ether, a polyester resin, a fluororesin, polyphenylene sulfide, polysulfone, polyallylate, polyether imide, polyether sulfone, polyether ketone, polyamideimide, polyallyl ether nitrile, polybenzimidazole, and a metal foil; and composite sheets produced by combining these films can be considered.

Among these, in order to prevent deformation such as curling effectively, the thermal shrinkage in the longitudinal direction and the transverse direction is preferably less than 1%, and more preferably 0.5% or less.

Particularly, in the case of imparting transparency, a support formed include a polymer film is preferred. Examples thereof include synthetic polymer films including polyester films such as polyethylene terephthalate, polybutylene terephthalate, and polyethylene naphthalate; cellulose triacetate film; and polyolefin films such as polypropylene and polyethylene. Among them, a support of polyethylene naphthalate (PEN) or polyimide (PI) having high temperature resistance is preferred.

Furthermore, when the synthetic polymer film is transparent, the film may be colored in any color. Examples of the method of coloring a synthetic polymer film include a method of kneading a dye with a resin before a resin film is molded, and molding a film; a method of preparing a coating liquid in which a coloring pigment is dispersed, and applying the coating liquid on a support; and a method of preparing a coating liquid in which a dyestuff is dissolved in an appropriate solvent, and applying this coating liquid on a colorless transparent resin film by a known coating method, for example, a curtain coating method, a die coating method, a gravure coating method, a roller coating method, or a wire coating method.

<Other Layer>

The thermal distribution display of the invention may include, in addition to the thermal distribution display layer, other layers such as a protective layer, an intermediate layer, an undercoat layer, a light reflective layer, a back layer, and an ultraviolet absorbing layer, to the extent that the effects of the invention are not impaired.

Among the other layers described above, the light reflective layer contains at least a pigment, and preferably contains a white pigment. As a light reflective layer is provided on the thermal distribution display layer, when observed from the upper side of the support surface, the color developing section is viewed clearly, and the differences in the density or hue of the thermal distribution can be easily observed.

Suitable examples of the pigment include inorganic pigments such as titanium oxide, kaolin, aluminum hydroxide, amorphous silica, and zinc oxide.

Furthermore, the light reflective layer can contain a binder together with a pigment, and may further contain a crosslinking component that crosslinks the binder. The binder is preferably a water-soluble polymer compound such as gelatin or polyvinyl alcohol. In this case, when the light reflective layer further contains a crosslinking agent to crosslink the binder, storage stability can be further enhanced. The crosslinking agent may be appropriately selected from known crosslinking agents. Examples thereof include water-soluble initial condensates such as N-methylolurea, N-methylolmelamine, and urea-formalin; dialdehyde compounds such as glyoxal and glutaraldehyde; inorganic crosslinking agents such as boric acid and borax; and polyamidoepichlorohydrin.

The thickness of the light reflective layer is not particularly limited, and is preferably 1.0 μm to 6.0 μm.

—Method for Producing Thermal Distribution Display—

The thermal distribution display of the invention can be produced by, for example, applying a coating liquid for thermal distribution display layer formation (hereinafter, referred to as "coating liquid for thermal distribution display layer") on one side of a support, and thereby forming a thermal distribution display layer. Furthermore, if necessary, a coating liquid for intermediate layer and a coating liquid for protective layer are applied on the thermal distribution display layer, and with or without this application, a back layer formed from a single layer or plural layers can be formed by applying a coating liquid for back layer on the reverse side of the relevant side, as described above. Also, if necessary, other layers may also be formed on the aforementioned side and the other side.

Here, the thermal distribution display layer, the intermediate layer and the protective layer may be formed simultaneously. In this case, these layers can be formed by multilayer applying a coating liquid for thermal distribution display layer, and coating liquids for intermediate layer and protective layer simultaneously on the support.

—Measurement or Confirmation of Thermal Distribution—

When the thermal distribution display of the invention is put to use, the thermal distribution display of the invention is disposed on, for example, a heated surface of a heated roller or a heated plate, and the thermal distribution display layer of the thermal distribution display is heated by the heat of the heated surface to develop color, an image is recorded in the thermal distribution display, and thus a thermal distribution can be understood. The thermal distribution display may be disposed to be in direct contact with the heated surface, or may be disposed between the heated surface and the thermal distribution display, with an intermediate body such as a sheet or a film interposed therebetween.

EXAMPLES

Hereinafter, the invention will be described more specifically by way of Examples, but the invention is not intended to be limited to the following Examples as long as the gist is maintained. Meanwhile, unless particularly stated otherwise, the unit "parts" is on a mass basis.

In addition, in the present Examples, the average particle size was measured with a laser diffraction particle size distribution analyzer, LA700 [manufactured by Horiba, Ltd.].

—Preparation of Microcapsules—

70 g of an electron-donating dye precursor selected from the following items (1) to (10) and 150 g of ethyl acetate were heated to 70° C. to melt, and then the melt was cooled to 45° C. To this, 100 g of the wall material described in the following Table 1 was added and mixed as a wall material, and thus a solution was obtained. This solution was added to an aqueous phase composed of 400 g of a 5.9 mass % aqueous solution of polyvinyl alcohol (manufactured by Kuraray Co., Ltd., PVA-217E), subsequently emulsifying dispersion was carried out at a speed of rotation of 3000 rpm using ROBOMIX (manufactured by Tokushu Kika Kogyo Co., Ltd.), and thus an emulsion liquid was obtained. 300 g of water and 10.0 g of tetraethylenepentamine were added to the emulsion liquid thus obtained, and then the mixture was subjected to an encapsulation reaction over 4 hours at a temperature of 60° C. Thereafter, water was added thereto to adjust the concentration to 22% by mass, and thus 20 kinds of dye precursor-containing microcapsule liquids A to T as indicated in the following Table 1 were prepared.

Meanwhile, in regard to the processes described above, the particle size was adjusted by setting the speed of rotation of ROBOMIX constant at 3000 rpm, and changing the time for performing emulsifying dispersion in the range of 2 minutes to 8 minutes.

Cyan Color Dye Precursors:

| | $R^1$ | $R^2$ | $R^3$ | $R^4$ | $R^5$ |
|---|---|---|---|---|---|
| (1) BLUE 220 (manufactured by Yamada Chemical Co., Ltd.) | $C_2H_5$ | $C_2H_5$ | $CH_3$ | $CH_3$ | $C_2H_5$ |
| (2) BLUE 4450 (manufactured by Yamamoto Chemicals, Inc.) | $C_3H_7$ | $C_3H_7$ | $NHCOCH_3$ | $CH_3$ | $C_8H_{17}$ |
| (3) PERGASCRIPT BLUE FT 2383 (manufactured by Ciba Geigy Japan, Ltd.) | $C_2H_5$ | $C_2H_5$ | $OC_2H_5$ | $CH_3$ | $C_8H_{17}$ |
| (4) BLUE 63 (manufactured by Yamamoto Chemicals, Inc.) | $C_2H_5$ | $C_2H_5$ | $OC_2H_5$ | $CH_3$ | $C_2H_5$ |

(5) Magenta Color Dye Precursor:
3,3'-Bis(1-n-octyl-2-methylindol-3-yl)phthalide (manufactured by Ciba Geigy Japan, Ltd., PERGASCRIPT RED I-6B)

(6) Yellow Color Dye Precursor:
1-(4-n-dodecyloxy-3-methoxyphenyl)-2-(2-quinolyl)ethylene (manufactured by Yamada Chemical Co., Ltd., Y721)

(7) Red Color Dye Precursor:
6'-[Ethyl(4-methylphenyl)amino]-2'-methylspiro[isobenzofuran-1(3H),9'-(9H)xanthene]-3-one (manufactured by Yamada Chemical Co., Ltd., RED 520)

(8) Orange Color Dye Precursor:
3'-Chloro-6'-(cyclohexylamino)-spiro[isobenzofuran-1 (3H),9'-(9H)xanthene]-3-one (manufactured by BASF Japan, Ltd.; PERGASCRIPT ORANGE I-G)

(9) Blue Color Dye Precursor:
Crystal Violet Lactone (manufactured by Hilton Davis Chemical Co.; COPIKEM1)

(10) Black Color Dye Precursor:
2-Anilino-6-(N-ethyl-N-isobutylamino)-3-methylfluoran (manufactured by Yamada Chemical Co., Ltd., S-204)

—Measurement of Tg of Various Capsule Walls of Microcapsule Liquids—

For the microcapsule liquids obtained as described above, the glass transition temperature (Tg) of each capsule wall was measured using EXSTAR6000 (manufactured by Seiko Instruments, Inc.). The measurement results are presented in the following Table 1.

TABLE 1

| No. | Electron-donating dye precursor | Wall material | Particle size [μm] | Tg [° C.] |
|---|---|---|---|---|
| A | (1) | TAKENATE D110N (manufactured by Mitsui Takeda Chemicals, Inc.) | 2.8 | 142 |
| B | (2) | TAKENATE D110N (manufactured by Mitsui Takeda Chemicals, Inc.) | 3.1 | 145 |
| C | (3) | TAKENATE D110N (manufactured by Mitsui Takeda Chemicals, Inc.) | 1.9 | 140 |
| D | (4) | TAKENATE D110N (manufactured by Mitsui Takeda Chemicals, Inc.) | 3.5 | 148 |
| E | (5) | TAKENATE D110N (manufactured by Mitsui Takeda Chemicals, Inc.) | 2.8 | 153 |
| F | (6) | TAKENATE D110N (manufactured by Mitsui Takeda Chemicals, Inc.) | 2.2 | 143 |
| G | (7) | TAKENATE D110N (manufactured by Mitsui Takeda Chemicals, Inc.) | 3.3 | 149 |
| H | (8) | TAKENATE D110N (manufactured by Mitsui Takeda Chemicals, Inc.) | 3.4 | 145 |
| I | (9) | TAKENATE D110N (manufactured by Mitsui Takeda Chemicals, Inc.) | 2.8 | 143 |
| J | (10) | TAKENATE D110N (manufactured by Mitsui Takeda Chemicals, Inc.) | 3.1 | 147 |
| K | (1) | TAKENATE D110N (manufactured by Mitsui Takeda Chemicals, Inc.)/ BURNOCK D750 (manufactured by Dainippon Ink and Chemicals, Inc.) = 50/50 | 2.5 | 175 |
| L | (2) | TAKENATE D110N (manufactured by Mitsui Takeda Chemicals, Inc.)/ MILLIONATE MR400 (manufactured by Nippon Polyurethane Industry Co., Ltd.) = 50/50 | 3.3 | 171 |
| M | (5) | TAKENATE D110N (manufactured by Mitsui Takeda Chemicals, Inc.)/ BURNOCK D750 (manufactured by Dainippon Ink and Chemicals, Inc.) = 50/50 | 2.8 | 169 |
| N | (6) | (N) TAKENATE D110N (manufactured by Mitsui Takeda Chemicals, Inc.)/ MILLIONATE MTL (manufactured by Nippon Polyurethane Industry Co., Ltd.) = 50/50 | 3.2 | 174 |
| O | (7) | (O) TAKENATE D127N (manufactured by Mitsui Takeda Chemicals, Inc.) | 3.9 | 170 |
| P | (9) | (P) TAKENATE D110N (manufactured by Mitsui Takeda Chemicals, Inc.)/ MILLIONATE MR400 (manufactured by Nippon Polyurethane Industry Co., Ltd.) = 50/50 | 3.5 | 177 |
| Q | (10) | (Q) TAKENATE D110N (manufactured by Mitsui Takeda Chemicals, Inc.)/ BURNOCK D750 (manufactured by Dainippon Ink and Chemicals, Inc.) = 50/50 | 3.8 | 174 |
| R | (1) | (R) TAKENATE D110N (manufactured by Mitsui Takeda Chemicals, Inc.)/ BURNOCK D750 (manufactured by Dainippon Ink and Chemicals, Inc.) = 75/25 | 2.9 | 196 |
| S | (4) | (S) TAKENATE D110N (manufactured by Mitsui Takeda Chemicals, Inc.)/ MILLIONATE MR200 (manufactured by Nippon Polyurethane Industry Co., Ltd.) = 85/15 | 3.3 | 201 |
| T | (10) | (T) TAKENATE D110N (manufactured by Mitsui Takeda Chemicals, Inc.)/ BURNOCK D750 (manufactured by Dainippon Ink and Chemicals, Inc.) = 80/20 | 1.8 | 204 |

Examples 1 to 9

Preparation of Coating Liquid for Light Reflective Layer (1) Preparation of Pigment Dispersion Liquid for Light Reflective Layer 50 g of titanium oxide (manufactured by Ishihara Sangyo Kaisha, Ltd., R780-2), 0.6 g of polycarboxylic acid (manufactured by Kao Corp., DEMOL EP) at a concentration of 25% by mass, and 70 g of a 8.0 mass % aqueous solution of polyvinyl alcohol (manufactured by Kuraray Co., Ltd., PVA-205 (degree of saponification: 88%)) were mixed, and titanium oxide was dispersed therein. Furthermore, the dispersion was pulverized using a sand mill, and thus a pigment dispersion liquid for light reflective layer having an average particle size of 0.35 μm was prepared.

(2) Preparation of Coating Liquid for Light Reflective Layer 30 g of the pigment dispersion liquid for light reflective layer, 90 g of a 5.0 mass % aqueous solution of polyvinyl alcohol (manufactured by Adeka Corp., EP-130), 5 g of 4.0 mass % boric acid, and 2.0 g of 2.0 mass % sodium dodecyl benzenesulfonate were mixed, and thus a coating liquid for light reflective layer was obtained.

Preparation of Coating Liquid for Thermal Distribution Display Layer 25 g of a 42.5 mass % aqueous suspension of salicylic acid zinc salt (compound 1-1) having a structure described below (manufactured by Sanko Co., Ltd., LR-220) as an electron-accepting compound, 20 g of a dye precursor-containing microcapsule liquid (I) indicated in the following Table 2, 20 g of a dye precursor-containing microcapsule liquid (II) indicated in the following Table 2, 50 g of a 5 mass % aqueous solution of polyvinyl alcohol (manufactured by Adeka Corp., EP-130), 0.25 g of glyoxal, and 0.1 g of a 50 mass % fluorescent brightening agent (manufactured by Nippon Kayaku Co., Ltd., KAYAHOR S) were mixed, and thus a coating liquid for thermal distribution display layer was prepared.

Compound (1-1)

Production of Thermal Distribution Display Material

On one surface of a transparent polyethylene naphthalate support (manufactured by Teijin, Ltd., TEONEX Q51; referred to as "PEN support") having a thickness of 75 μm, the coating liquid for thermal distribution display layer and the coating liquid for light reflective layer were sequentially applied such that the solid content amounts would be 4.0 g/m² and 4.0 g/m², respectively, and the coating liquids were dried. Thus, a thermal distribution display material was produced.

Examples 10 and 11

Thermal distribution display materials were produced in the same manner as in Example 1, except that the coating liquid for thermal distribution display layer used in Example 1 was replaced with a coating liquid for thermal distribution display layer described below that used three kinds of dye precursor-containing microcapsule liquids. Here, the amounts of coating of the coating liquid for thermal distribution display layer and the coating liquid for light reflective layer were set to 5.5 g/m² and 4.0 g/m², respectively.

Preparation of Coating Liquid for Thermal Distribution Display Layer 25 g of a 42.5 mass % aqueous suspension of salicylic acid zinc salt (compound 1-1) having a structure described below (manufactured by Sanko Co., Ltd., LR-220) as an electron-accepting compound, 15 g of a dye precursor-containing microcapsule liquid (I) indicated in the following Table 2, 15 g of a dye precursor-containing microcapsule liquid (II) indicated in the following Table 2, 15 g of a dye precursor-containing microcapsule liquid (III) indicated in the following Table 2, 50 g of a 5 mass % aqueous solution of polyvinyl alcohol (manufactured by Adeka Corp., EP-130), 0.25 g of glyoxal, and 0.1 g of a 50 mass % fluorescent brightening agent (manufactured by Nippon Kayaku Co., Ltd., KAYAHOR S) were mixed, and thus a coating liquid for thermal distribution display layer was prepared.

Comparative Examples 1 to 3

Comparative thermal distribution display materials were produced in the same manner as in Examples 1, 3 and 6, except that 25 g of the 42.5 mass % aqueous suspension of salicylic acid zinc salt (compound 1-1) (LR-220) that was used in the preparation of the coating liquid for thermal distribution display layer in Examples 1, 3 and 6 was replaced with 35 g of an electron-accepting compound dispersion liquid described below.

Preparation of Electron-Accepting Compound Dispersion Liquid 60 g of 4-[[4-(1-methylethoxy)phenyl]sulfonyl]phenol (manufactured by Nippon Soda Co., Ltd., D-8) and 140 g of an aqueous solution of partially saponified polyvinyl alcohol (manufactured by Kuraray Co., Ltd., PVA-205) at a concentration of 5% by mass were stirred while the mixture was pulverized using a sand mill. Thus, an electron-accepting compound dispersion liquid having an average particle size of 0.6 μm was prepared.

Comparative Example 4

A comparative thermal distribution display material was obtained in the same manner as in Example 1, except that the dye precursor-containing microcapsule liquid A used as the dye precursor-containing microcapsule liquid (I) in Example 1 was replaced with the dye precursor-containing microcapsule liquid I.

Comparative Examples 5 to 7

Comparative thermal distribution display materials were produced in the same manner as in Example 1, except that the coating liquid for thermal distribution display layer used in Example 1 was replaced with a coating liquid for thermal distribution display layer described below that used only one kind of dye precursor-containing microcapsule liquid as indicated in the following Table 2. Here, the amounts of coating of the coating liquid for thermal distribution display layer and the coating liquid for light reflective layer were set to 3.0 g/m² and 4.0 g/m², respectively.

Preparation of Coating Liquid for Thermal Distribution Display Layer 25 g of a 42.5 mass % aqueous suspension of salicylic acid zinc salt (compound 1-1) having a structure described below (manufactured by Sanko Co., Ltd., LR-220) as an electron-accepting compound, 30 g of a dye precursor-containing microcapsule liquid (I) indicated in the following Table 2, 50 g of a 5 mass % aqueous solution of polyvinyl alcohol (manufactured by Adeka Corp., EP-130), 0.25 g of glyoxal, and 0.1 g of a 50 mass % fluorescent brightening agent (manufactured by Nippon Kayaku Co., Ltd., KAYAHOR S) were mixed, and thus a coating liquid for thermal distribution display layer was prepared.

Evaluation

The thermal distribution displays obtained as described above were each brought into contact for 10 seconds with a heat source using a ten serial type thermal characteristics testing machine (manufactured by Shinto Scientific Co., Ltd.), while temperature was changed at an interval of 10° C. in a temperature range of from 130° C. to 220° C. Thereafter, the density of the color developed was measured with a Macbeth densitometer (RD-918, manufactured by GretagMacbeth AG), and at the same time, the temperature range in which the difference of color and the difference of density can be visually recognized for each of the developed colors was investigated. The results are presented in the following Table 2.

TABLE 2

| | Material No. | Microcapsule liquid (I) | (II) | (III) | 0.2 ($T_{0.2}$ − Tmin) | 130 to 160° C. | 160 to 190° C. | 190 to 220° C. | Temperature range enabling visualization ° C. |
|---|---|---|---|---|---|---|---|---|---|
| Example 1 | (1) | A | M | — | 0.011 | Cyan to blue | Blue to violet | Violet to pink | 140 to 210 |
| Example 2 | (2) | B | M | — | 0.013 | Cyan to blue | Blue to violet | Violet to pink | 140 to 210 |
| Example 3 | (3) | E | K | — | 0.015 | Magenta | Magenta to violet | Violet to pink | 150 to 210 |
| Example 4 | (4) | C | N | — | 0.009 | Cyan to blue green | Blue green to green | Green to yellow | 140 to 200 |
| Example 5 | (5) | D | P | — | 0.011 | Cyan to light blue | Light blue to blue | Blue to green | 140 to 200 |
| Example 6 | (6) | A | O | — | 0.012 | Cyan to violet | Violet to red | Red to pink | 150 to 210 |
| Example 7 | (7) | G | L | — | 0.015 | Red to violet | Violet to blue | Blue to orange | 140 to 200 |
| Example 8 | (8) | B | Q | — | 0.011 | Cyan to grey | Grey to black | Black to brown | 140 to 200 |
| Example 9 | (9) | H | K | — | 0.01 | Orange to grey | Grey to black | Black to orange | 150 to 200 |
| Example 10 | (10) | F | L | R | 0.007 | Yellow to yellow green | Yellow green to black | Black to red | 130 to 220 |
| Example 11 | (11) | F | M | S | 0.008 | Yellow to pink | Pink to red violet | Black to red | 130 to 220 |
| Comparative Example 1 | (12) | A | M | — | 0.038 | Cyan to violet | Violet | Violet to pink | 140 to 170 |
| Comparative Example 2 | (13) | E | K | — | 0.045 | Magenta to violet | Violet | Violet to red | 140 to 160 |
| Comparative Example 3 | (14) | A | O | — | 0.033 | Cyan to red | Red | Red to pink | 140 to 160 |
| Comparative Example 4 | (15) | I | M | — | 0.015 | Blue to violet | Violet to red violet | Red violet | 140 to 170 |
| Comparative Example 5 | (16) | J | — | — | 0.034 | Grey to black | Black | Black | 130 to 150 |
| Comparative Example 6 | (17) | Q | — | — | 0.029 | White | Grey to black | Black | 160 to 180 |
| Comparative Example 7 | (18) | T | — | — | 0.024 | White | White | Grey to black | 200 to 220 |

Figure 1:
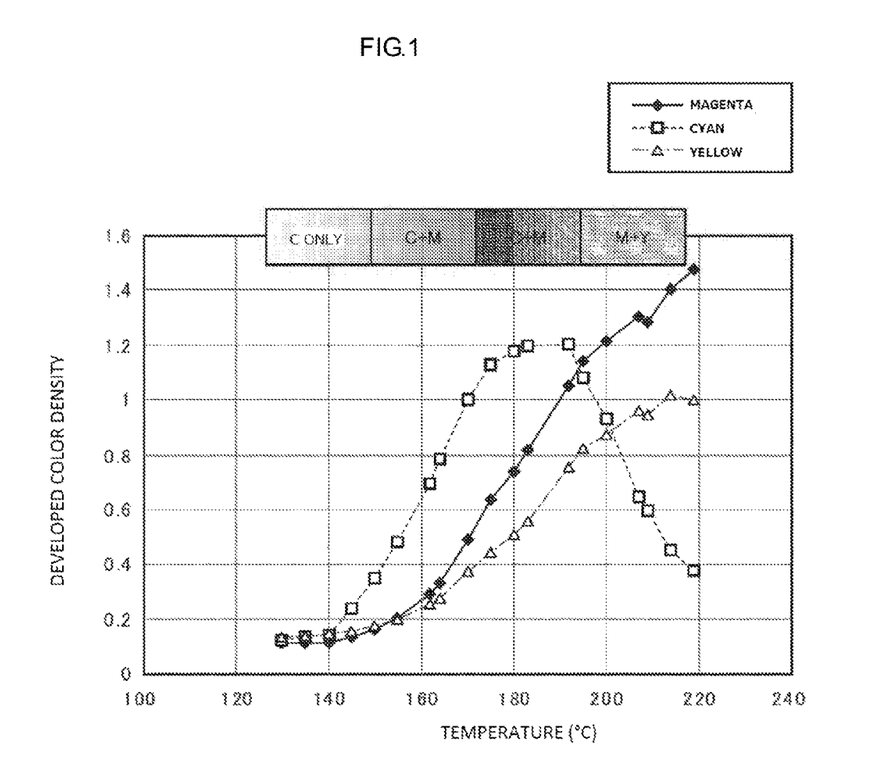
FIG. 1 is a graph illustrating color development characteristics of a thermal distribution display material of Example 1.

As shown in the above Table 2, in the Examples, developed colors with different hues were obtained to a visually recognizable extent, in a wide temperature range extending from 130° C. to 220° C., and thermal distributions with wide temperature ranges compared with conventional cases could be measured. For example, in Example 1, the color development characteristics shown in FIG. 1 are exhibited. Thereby, a thermal distribution display is enabled with multiple colors as shown in column A of FIG. 2. That is, in the case of Example 1, a thermal distribution is displayed by the shades of cyan color in a temperature range of 130° C. to 160° C., and a thermal distribution is displayed by a change in hue of blue to violet as a result of mixing cyan color with magenta color in a temperature range of 160° C. to 190° C. Furthermore, it is understood that in a temperature range of 190° C. to 220° C., 4-azaphthalide (for example, the cyan color dye precursor (1) in Example 1) is thermally decomposed and exhibits yellow color, and a thermal distribution is displayed by a further change in hue of violet to pink. As such, since changes in hue are obtained in a high temperature range of 190° C. or higher as a result of color development by thermal decomposition of the electron-donating dye precursors, a thermal distribution with (n+1) colors is exhibited in a high temperature region of from near 130° C. to 200° C. or higher, with n kinds of dye precursors corresponding to the development of n colors. Thereby, measurement of a thermal distribution is enabled over a temperature region that is wider than the conventional cases, including a high temperature region.

On the contrary, in Comparative Examples, it was difficult to secure a wide thermal distribution range that could be measured. Here, the thermal distributions obtained in Comparative Examples 5 and 6 will be shown in column B of FIG. 2 and column C of FIG. 2, respectively. The thermal distribution display material of Comparative Example 5 had a higher y value in a temperature range of 140° C. to 160° C., and as shown in column B of FIG. 2, shades are seen in temperature range of 130° C. to near 150° C.; however, when the temperature reaches near 150° C. to 160° C., the thermal distribution display material exhibited an almost black color, so that the presence or absence of thermal change could not be displayed thereafter. Here, the temperature range that could be displayed was 130° C. to 160° C. Furthermore, the thermal distribution display material of Comparative Example 6 had a high y value in the temperature of 160° C. to 180° C., and as shown in column C of FIG. 2, when the temperature reached near 190° C., the thermal distribution display material exhibited an almost black color, so that the presence or absence of thermal change could not be display thereafter. Here, the temperature range that could be displayed was 140° C. to 190° C.

Example 12

A thermal distribution display material was produced in the same manner as in Example 1, except that the amount of the dye precursor-containing microcapsule liquid (I) used in the preparation of the coating liquid for thermal distribution display layer in Example 1 was changed from 20 g to 13 g, the amount of the dye-precursor-containing microcapsule liquid (II) was changed from 20 g to 26 g, and the content ratio of the cyan color dye precursor and the magenta color dye precursor (cyan/magenta ratio [mass ratio]) was changed to 1/2.

As a result, as shown in column D of FIG. 2, although the color development temperature and the hue of the developed color were slightly different, a thermal distribution display could be made over a wide temperature range including a high temperature range (a range from near 140° C. to 200° C. or higher), as in the case of Example 1.

Example 13

A thermal distribution display material was produced in the same manner as in Example 1, except that the amount of the dye precursor-containing microcapsule liquid (I) used in the preparation of the coating liquid for thermal distribution display layer in Example 1 was changed from 20 g to 26 g, the amount of the dye-precursor-containing microcapsule liquid (II) was changed from 20 g to 13 g, and the content ratio of the cyan color dye precursor and the magenta color dye precursor (cyan/magenta ratio [mass ratio]) was changed to 2/1.

As a result, as shown in column E of FIG. 2, although the color development temperature and the hue of the developed color were slightly different, a thermal distribution display could be made over a wider temperature range including a high temperature range as in the case of Example 1. In the present Example in which the cyan/magenta ratio was 2/1, even clearer changes in hue were exhibited as compared with Example 1, and a thermal distribution was clearly displayed over a temperature range of near 130° C. to 220° C.

Here, in column A, column D and column E of FIG. 2, the ranges in which the electron-donating dye precursors that decompose in a temperature range of 190° C. or higher and undergo a change in hue exhibited hues that were different from the hues developed by a reaction with the electron-accepting compound as a result of thermal decomposition, and this exhibition could be confirmed, were indicated by hatching.

INDUSTRIAL APPLICABILITY

The thermal distribution display of the invention can be suitably used in the fields where planar heating is applied by hot pressing or the like, such as bonding of anisotropic conductive films (ACF), heat sealing, or bonding of electronic components such as flexible printed circuit boards (FPC), and in the management of a drying furnace for baking finish, and the like.

The invention claimed is:

1. A thermal distribution display comprising, on a support, a thermal distribution display layer that comprises: at least two electron-donating dye precursors that develop mutually different color tones, the dye precursors including at least one electron-donating dye precursor that decomposes in a temperature range of 190° C. or higher to undergo a change in hue; at least one electron-accepting compound that allows the at least two electron-donating dye precursors to develop colors; and a binder, wherein, in the thermal distribution display layer, a temperature $T_{0.2}$, at which a density is 0.2 greater than a background density, satisfies the following formula (1):

$$\frac{0.2}{T_{0.2} - T_{min}} \leq 0.02 \qquad \text{Formula (1)}$$

wherein, in formula (1), $T_{0.2}$ represents a temperature [° C.] at which the density is 0.2 greater than a background density ($D_{min}$); and $T_{min}$ represents a color development initiation temperature [° C.], and wherein the at least one electron-donating dye precursor that decomposes in a temperature range of 190° C. or higher to undergo a change in hue is an indolylazaphthalide compound represented by the following formula (a):

Formula (a)

wherein, in formula (a), each of $R^1$, $R^2$, $R^3$, $R^4$ and $R^5$ independently represents a hydrogen atom, an alkyl group, a cycloalkyl group, an aralkyl group, an aryl group, a carbamoyl group, an alkoxy group, or a heterocyclic group.

2. The thermal distribution display according to claim 1, wherein the at least two electron-donating dye precursors are respectively encapsulated in microcapsules formed from wall materials having mutually different glass transition temperatures.

3. The thermal distribution display according to claim 1, wherein the at least one electron-accepting compound is a compound represented by the following formula (b):

Formula (b)

wherein, in formula (b), each of $R^1$, $R^2$, $R^3$ and $R^4$ independently represents a hydrogen atom, a halogen atom, an amino group, a carboxyl group, a carbamoyl group, a hydroxyl group, an alkylsulfonyl group, an alkyl group, or an aryl group, while any adjacent two of $R^1$ to $R^4$ may be bonded to each other and form a cyclic structure; M represents an n-valent metal atom; and n represents an integer from 1 to 3.

4. The thermal distribution display according to claim 1, wherein the microcapsules have walls of a polymer having at least one of a urethane bond or a urea bond.

5. The thermal distribution display according to claim 1, comprising, as the at least two electron-donating dye precursors, the indolylazaphthalide compound represented by formula (a) that develops cyan color, and an electron-donating dye precursor that develops magenta color.

6. The thermal distribution display according to claim 5, wherein a mass content ratio of the indolylazaphthalide compound represented by formula (a) that develops cyan color and the electron-donating dye precursor that develops magenta color is from 1/2 to 2/1.

7. The thermal distribution display according to claim 5, wherein the indolylazaphthalide compound and the electron-donating dye precursor are respectively encapsulated in microcapsules formed from wall materials having glass transition temperatures that are mutually different and that are lower than 220° C.

8. The thermal distribution display according to claim 1, comprising a light reflective layer on the thermal distribution display layer provided on the support.

* * * * *